United States Patent [19]
Cota

[11] Patent Number: 6,024,723
[45] Date of Patent: Feb. 15, 2000

[54] REMINDER DEVICE FOR BLOOD SELF-TESTING

[76] Inventor: Joseph A. Cota, Apt #1, No. Andover, Mass. 01845

[21] Appl. No.: 09/262,511

[22] Filed: Mar. 4, 1999

[51] Int. Cl.$^7$ ..................................................... A61M 5/00
[52] U.S. Cl. ......................... 604/116; 116/200; 116/306; 116/311; 116/315
[58] Field of Search ............................ 604/116; 116/121, 116/223, 224, 306, 311, 315, 325; 40/110, 657

[56] References Cited

U.S. PATENT DOCUMENTS

| | | | |
|---|---|---|---|
| 2,984,033 | 5/1961 | Sampson . | |
| 3,547,121 | 12/1970 | Cherry | 128/215 |
| 3,852,900 | 12/1974 | Svec | 40/70 |
| 3,905,547 | 9/1975 | Cyre et al. | 235/90 |
| 3,996,471 | 12/1976 | Fletcher et al. | 250/444 |
| 3,999,504 | 12/1976 | Kearse | 116/121 |
| 4,228,796 | 10/1980 | Gardiner | 128/215 |
| 4,308,678 | 1/1982 | Slobin | 40/113 |
| 4,362,157 | 12/1982 | Keeth | 128/215 |
| 4,798,212 | 1/1989 | Arana | 604/116 |
| 4,854,061 | 8/1989 | Khoshkish | 40/495 |
| 4,905,388 | 3/1990 | Sinkow | 40/110 |
| 5,109,789 | 5/1992 | Berman | 116/325 |
| 5,377,614 | 1/1995 | Glazer | 116/308 |
| 5,613,463 | 3/1997 | Stokes | 116/315 |

*Primary Examiner*—Wynn Wood Coggins
*Assistant Examiner*—Michael M Thompson
*Attorney, Agent, or Firm*—Mark P. White

[57] ABSTRACT

A device is described for reminding a patient suffering from ailments such as diabetes and high cholesterol levels, who performs daily blood tests, of the site of the last blood extraction, in the case where blood is drawn from one or more sites of each finger of the hands. The invention includes two disks, each having an inner face and an outer face, the inner face containing a representation of the opposite hand from the other. On each disk finger holes are punched in the vicinity of the fingers to represent the sites where blood is drawn. On the inner face of each disk is a red marker area which may be displayed under the finger hole on the opposite disk, corresponding to the last site where blood was drawn. When the user progresses from one hand to the other in his testing regime, the device is flipped over, and the outside face of the other disk is used to display the status of the site where blood has been drawn on a representation of the hand currently used.

16 Claims, 4 Drawing Sheets

6,024,723

REMINDER DEVICE FOR BLOOD SELF-TESTING

BACKGROUND OF THE INVENTION

1. Field of the Invention

The present invention relates to medical reminder devices, and more specifically to reminders used in connection with the drawing of blood for self-testing by patients suffering from ailments such as diabetes and high cholesterol levels.

2. Description Relative to the Prior Art

Millions of people suffer from diabetes in the United States alone. Many of these patients are required to draw blood on a daily basis, and do test the blood themselves in order to assure the chemical balance of their systems, which is essential to their well-being.

Drawing of the blood involves puncturing the skin in the region where blood will flow freely and profusely. The fingers of the hands are generally chosen as appropriate for the sites of blood extraction.

Patients requiring this self testing will generally start with the thumb or little finger of one hand, draw blood from first one side of the finger and then the other, and proceed to the next finger, etc., until both sides of each finger have been used. The patient will then proceed to the other hand and repeat the process. When both side of each finger of the other hand have been used, the patient may again return to the first hand used, and repeat the process indefinitely.

However, after repeated testing, the fingers become sore, and the patient may become confused about which fingers have been recently used, and which have not. Repeatedly drawing blood from the same site is not only painful, it may lead to infections and other serious complications. If the patient's memory is not sufficient, some reminder device may be required to manage the testing process.

The current invention provides a simple, inexpensive, and easy-to-use device to take the guesswork out of testing.

SUMMARY OF THE INVENTION

A general object of the current invention is to provide a simple, low cost easy-to-use reminder to indicate the sites where blood has last been drawn for diabetes patients doing blood self-testing on a regular basis.

According to one aspect of the invention, the blood self-test reminder, used in conjunction with the drawing of blood from the one or more test areas on the fingers of the hand, includes a first disk, having an inside face and an outside face. The inside face contains a marker area, and the outside face contains a representation of a human hand with fingers. Near each finger representation one or more exposure areas appear. Also included is a second disk, having an inside face and an outside face, which is the mirror image of the first disk. The two disks are rotatingly affixed to each other. In use, one of the disks is rotated to a position in which the marker area of the other disc is displayed in the exposure area corresponding to the last finger tested.

In accordance with a second aspect of the invention, means are further included to maintain the disk in its then current position, until sufficient force is exerted to move the disk to a new position.

In accordance with a third aspect of the invention, means to maintain the disk in its then current position, until sufficient force is exerted to move the disk to a new position are further included.

In accordance with a fourth aspect of the invention, the marker area is of a size and position so that the marker is displayed beneath all the exposure areas on one side of a radius formed between the center of the disk and point on the circumference of the disk. As a result the exposure areas represent all of the test areas previously used.

In accordance with a fifth aspect of the invention a blood self-test reminder, used in conjunction with the drawing of blood from the one or more test areas on the fingers of both hands, includes a base, having a first side and a second side, each side containing a marker area. It further includes two disks, each rotatingly affixed to the base, one disk containing a representation of the left human hand, and the other containing a representation of the right human hand. Each disk contains one or more exposure areas on each finger of each hand representation, through which the marker areas are viewed. The user may rotate each disk to a position in which the marker area is displayed in the exposure area corresponding to the last finger tested.

According to a final aspect of the invention an annulus of high-friction material, concentric with the disk, having a radius substantially less than that of the disk, and affixed to the base between the disk and the base is provided, allowing the device to retain its last indicated setting, until changed by the user.

BRIEF DESCRIPTION OF THE DRAWINGS

These, and further features of the invention, may be better understood with reference to the accompanying specification and drawings depicting the preferred embodiment, in which.

DETAILED DESCRIPTION OF THE PREFERRED EMBODIMENTS

Figure 4:
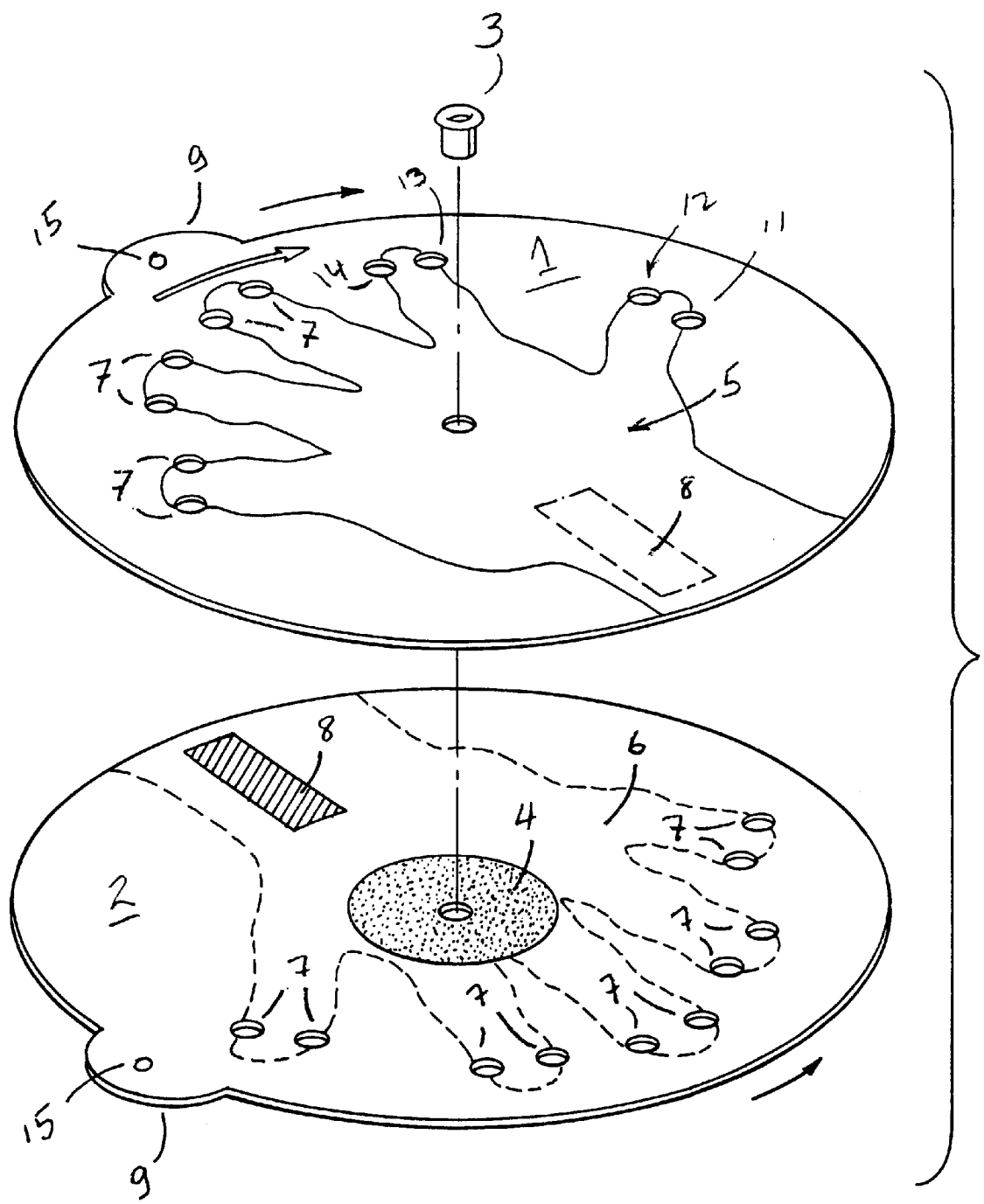
FIG. 4 depicts an exploded perspective view of an embodiment similar to that of FIG. 3, but having restricted marker areas which indicate only one finger hole of the opposite disk.

The preferred embodiments may be understood by first referring to FIG. 4, which depicts the invention as viewed from the front.

As seen in FIG. 4, the device, in its first preferred embodiment, consists of a first disk 1, and a second disk 2, attached to each other by a rivet 3, which passes through a hole at the center of each disk. These disks are made of paper, or of a thin, inexpensive plastic material. Each disk has an outside face and an inside face, the inside faces facing each other. Each inside face contains an annular area of high-friction materials that the disks will not freely slip, but will retain the last set position with respect to each other.

Still referring to FIG. 4, it is seen that the outside face of the first disk contains the representation of a human right hand 5, as seen from the palm, while the outside face of the second disk contains the representation of a human left hand 6. On the fingers of each hand representation are located a pair of finger holes 7, 11, 12, 13, 14. Also located on the inside face of each disk is a marker strip 8 of red colour, which is placed so that it may be seen on through one, and only one of the finger holes, depending upon the angle of rotation of the disks relative to each other.

Each disk further contains a tab 9, which the user may grasp when turning the disks relative to each other, and a peg hole 15, on which the device can be hung for storing when not in use.

In use, the user will select one hand or the other to begin the blood testing. Assuming, arguendo, that he chooses to being with the thumb of the left hand, he draws blood from the outside of the thumb, and then rotates the reminder so that marker strip 8 of the second disk 2 lies beneath finger hole 11 of the first disc 1. While this marker strip is typically a painted area of a color different from that of the rest of the inside faces of the disk, it may have other distinguishing characteristics, such as a cross-hatched pattern, etc..

The next time the user needs to draw blood, he refers to the reminder and notes that the marker strip is in view beneath finger hole 11, indicating that the outside thumb position has already been used. He then draws blood from the other side of the thumb, and rotates the reminder so that the marker strip is visible beneath finger hole 12.

The user may hang the reminder on a peg using the peg hole 15 in the tab 9, so that the face currently in use will be visible. When the user has drawn blood from the last position on the last finger of the right hand, he will begin with the thumb of the left hand. Then, he flips the reminder over, so that the outside of the second disk is visible, and, after drawing blood from the outside of the left thumb, aligns the disks so that the marker strip 8 of the first disk is visible beneath the appropriate finger hold of the second disk. The user will then hang the reminder on the peg with the outside face of the second disk in view.

The inside faces of each disk contain an annular area 4 which provides increased friction, preventing the two disks from turning freely, so that an angular setting, once made, will be maintained until the user desired it changed. This annular area may be textured to provide the increased friction. Alternatively, a sand-paper-like quality may be created by applying adhesive and then applying sand to the adhesive. Or a material such as sandpaper may be cut in the form of the annular area 4 shown in FIG. 4, and then affixing the annular area to the disks by adhesive means. The rivet 3 is inserted into the two disks, and then the open end folded over to capture the disks in close proximity to each other.

Figure 1:
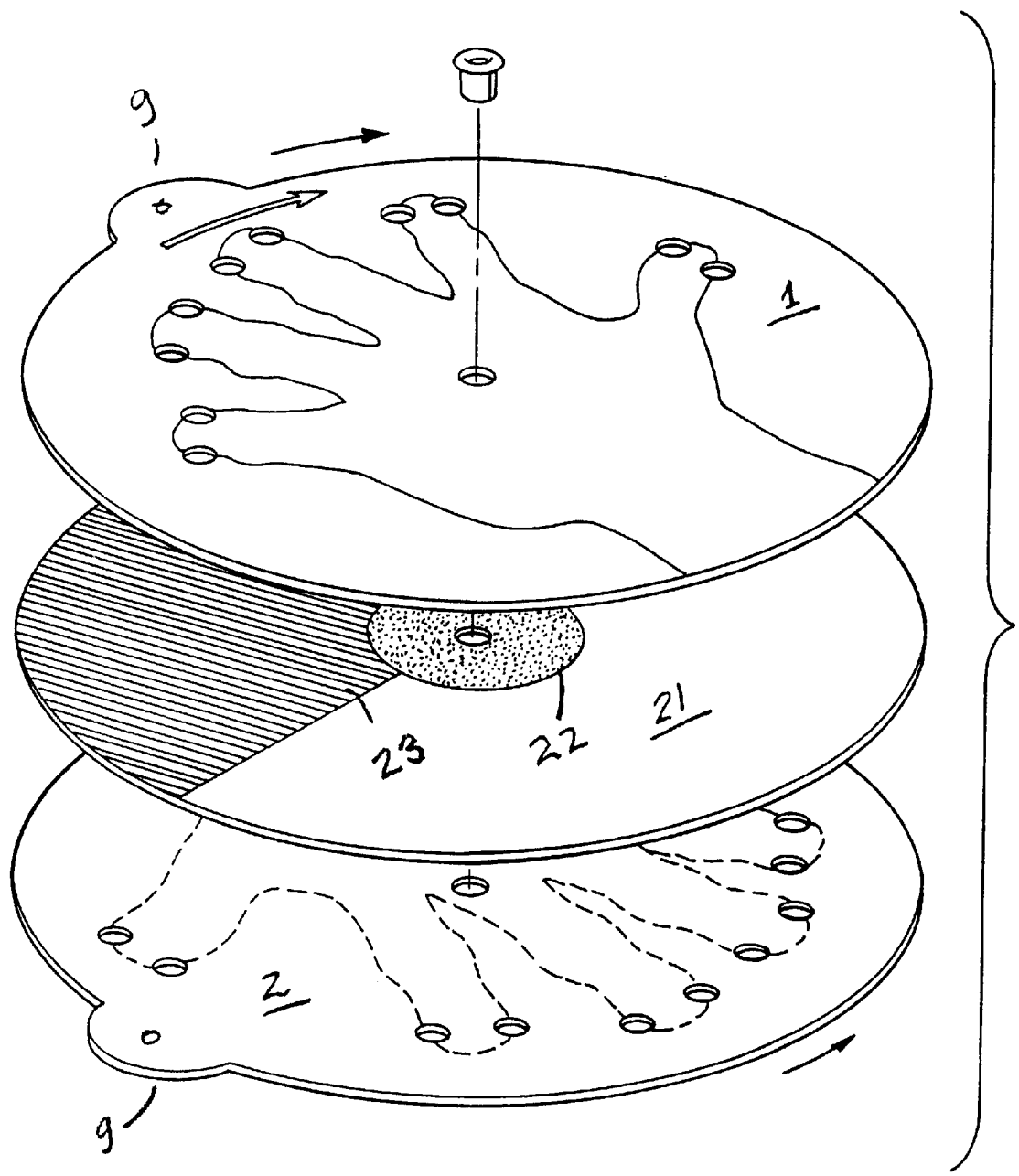
FIG. 1 depicts an exploded perspective view of an embodiment having two disks and a central base, and using friction means to maintain position of the disks relative to the base.
Figure 2:
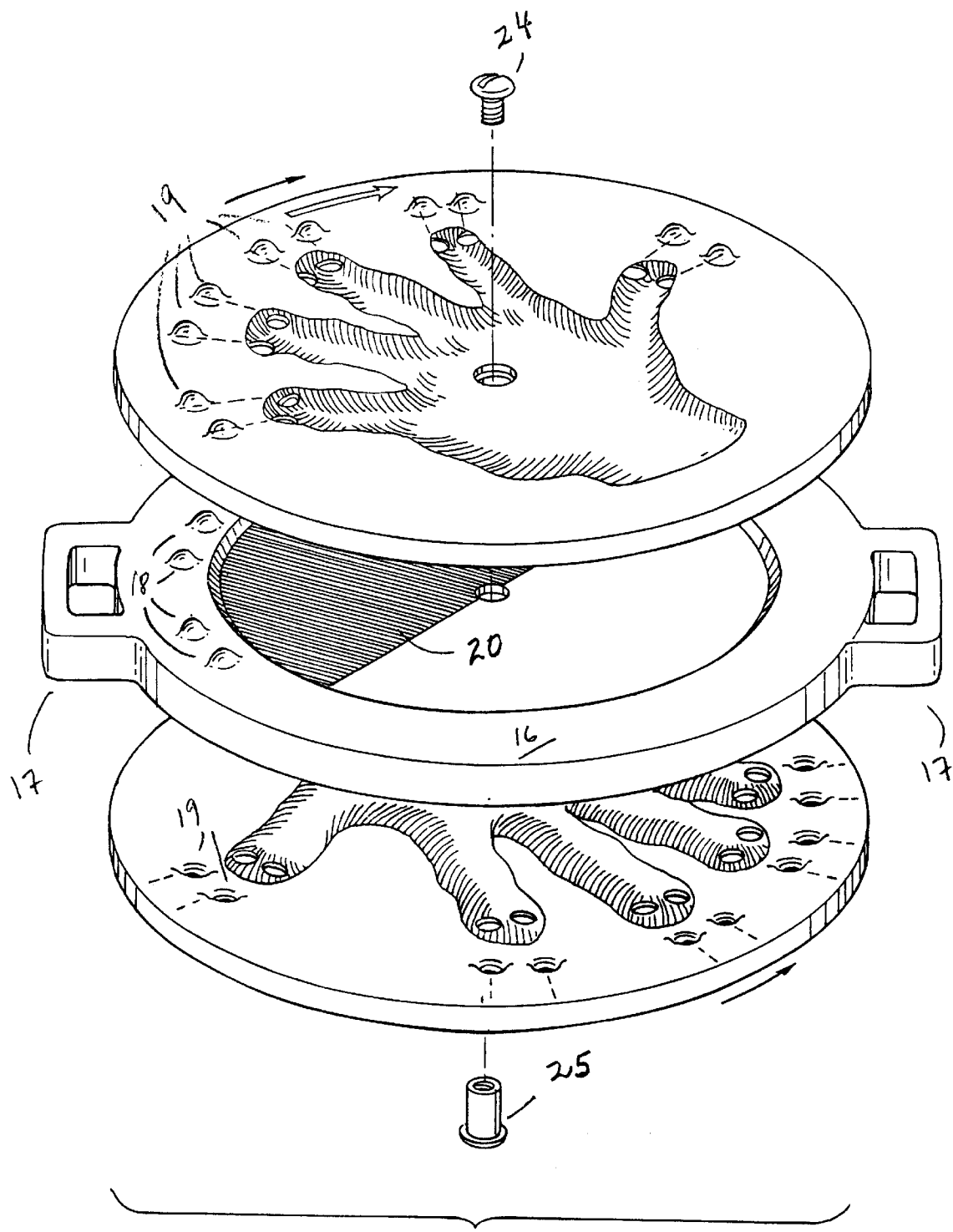
FIG. 2 depicts an exploded perspective view of an embodiment having two disks and a central base, of a heavier construction than the embodiment of FIG. 1, and using detent means to maintain position of the disks relative to the base.

A second preferred embodiment is depicted in FIG. 2. The embodiment shown in FIG. 2 shows a more complex structure than that of FIG. 1, and it is made of a thicker material than the paper of the first preferred embodiment. Plastic is anticipated for this embodiment, although other materials, such as metal, or wood, may also be used.

Still referring to FIG. 2, the device includes the two disks as in the first preferred embodiment, but also contains a base 16, with two faces, and which contains marker areas on both of its faces. This embodiment has tabs 17 located on the base, but they may also be included on the disks. The first and second disks containing the depiction of the hands do not have any markings on the inner face. This construction allows the two disks to be rotated relative to the base, but independently from each other.

The marker areas 20 for each hand in this embodiment extends so that all of the finger holes corresponding to the places where blood has already been drawn display the red colour of the marker area beneath. Using this embodiment, the user will never be in doubt as to whether he is proceeding from the thumb toward the little finger, or vice-versa. Furthermore, when all the fingers of one hand have been used, the user may leave that hand with all the finger holes showing red, so that there is no doubt which hand the user is testing.

The rivet of the first preferred embodiment has been replaced here by a more robust fastener, consisting of a machine screw 24 and a threaded sleeve 25. Furthermore, this embodiment uses male detents 18 on the central base, which mate with female detents 19 on the disks to maintain the position of the disks relative to the base, as opposed to the friction method of the first preferred embodiment.

Figure 3:
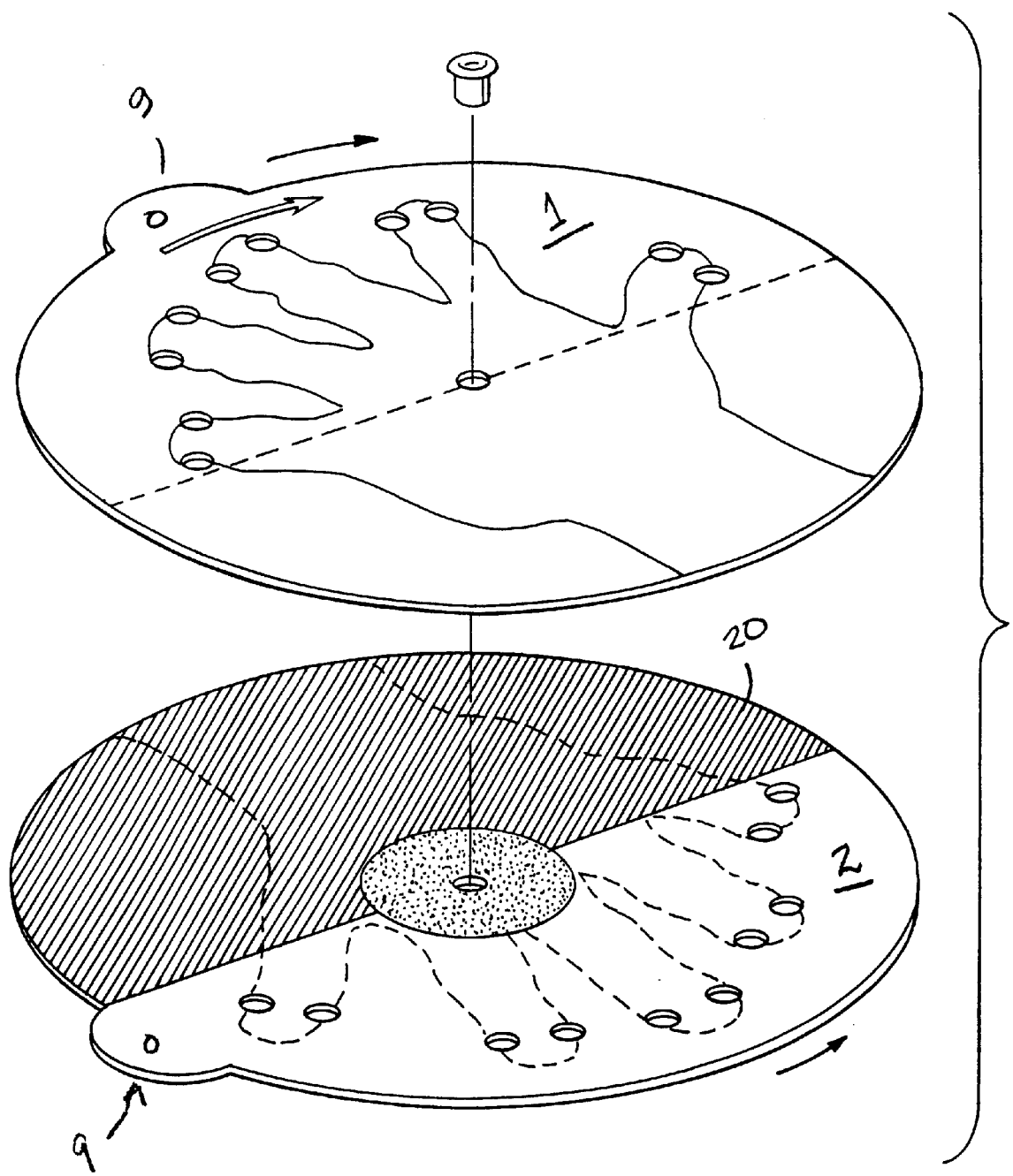
FIG. 3 depicts an exploded perspective view of an embodiment having two disks only, using friction means to maintain relative positions of the disks, and having extended marker areas on the inside faces on the disks.

The third preferred embodiment, as shown in FIG. 3, is similar to the first preferred embodiment. Like the first embodiment, this device is made of paper or similar material, contains only two disks and no central base, and uses friction to maintain the position of the disks relative to each other. However, in this embodiment the marker area 20 extends so that all of the finger holes corresponding to the areas on the users fingers already used for testing, are shown in red. Thus, there is no ambiguity in this embodiment as to whether the user is proceeding from the thumb to the little finger or vice versa. However, this embodiment will not disclose which hand is currently being tested, so the user must use other methods to so recall, such as leaving the reminder with the currently used face up.

The final embodiment, as shown in FIG. 1, is similar to the second embodiment of FIG. 2 in that it has a central base 21, and in that the marker area 23 extends to cover all the finger holes already used. The marker area appears on both sides of the central base. However, this final embodiment is also made of the thin paper-like material, and uses friction to maintain the position of the disks relative to each other. The high-friction ring 22 in this embodiment is located on both sides of the central base 21, rather than on the first and second disks themselves.

In a further embodiment, the hands may be displayed on an electronic device, with the blood extraction sites indicated electronically, by icons with distinctive shapes or colours to indicate that the site has been used or not used.

While the invention has been described with reference to specific embodiments, it will be apparent that improvements and modifications may be made within the purview of the invention without departing from the scope of the invention defined in the appended claims.

I claim:

1. A blood self-test reminder, used in conjunction with the drawing of blood from the one or more test areas on the fingers of the hand, comprising:

a first disk, having an inside face and an outside face, the inside face containing a marker area, and the outside face containing a representation of a human hand containing fingers, each finger representation having one or more exposure areas;

and a second disk, having an inside face and an outside face, rotatingly affixed to said first disk, the inside face containing a marker area, and the outside face containing a representation of the converse of the human hand represented on the first disc, each finger representation of the converse hand containing one or more exposure areas;

so that the user may rotate the disk to a position in which the marker area of one of the discs is displayed in the exposure area of the other disc, corresponding to the last finger tested.

2. The reminder in accordance with claim 1, further comprising means to maintain the disk in its then current position, until sufficient force is exerted to move the disk to a new position.

3. The reminder in accordance with claim 2, wherein the marker area are of a size and position so that the marker area is displayed beneath only one exposure area for each disk position.

4. The reminder in accordance with claim 2, wherein the marker area is of a size and position so that the marker is displayed beneath all the exposure areas on one side of a radius formed between the center of the disk and point on the circumference of the disk, and not displayed on any exposure area on the other side of the said radius, so that the exposure areas represent all of the test areas previously used.

5. A blood self-test reminder, used in conjunction with the drawing of blood from the one or more test areas on the fingers of both hands, comprising:

a base, having a first side and a second side, each side containing a marker area;
and two disks, each rotatingly affixed to said base, one disk containing a representation of a left human hand, and the other containing a representation of a right human hand, each disk containing one or more exposure areas on each finger of each hand representation, permitting viewing of said markers on said exposure areas, so that the user may rotate each disk to a position in which the marker area is displayed in the exposure area corresponding to the last finger tested.

6. The reminder in accordance with claim 5 further comprising means to maintain each disk in its then current position, until sufficient force is exerted to move the disk to a new position.

7. The reminder in accordance with claim 6, wherein each marker area is of a size and position so that the marker area is displayed beneath only one exposure area for each disk position of each disk.

8. The reminder in accordance with claim 6, wherein each marker area is of a size and position so that, for each disk, the marker area is displayed beneath all the exposure areas on one side of a radius formed between the center of the disk and point on the circumference of the disk, and not displayed on any exposure area on the other side of the said radius, so that, for each disk, the exposure areas represent all of the test areas previously used.

9. The reminder in accordance with claim 8, wherein the exposure areas consist of holes punched in the disk.

10. The reminder in accordance with claim 9, in which the disks and base are selected from a group consisting of paper, plastic, sheet metal, and wood.

11. The reminder in accordance with claim 10, in which the representations of the hands are selected from the group consisting of painting, impressing, embossing, printing, and molding.

12. The reminder in accordance with claim 11, wherein the means to maintain the position for each disk further comprises an annulus of high-friction material, concentric with the disk, having a radius substantially less than that of the disk, and located between the disk and the base.

13. The reminder in accordance with claim 11, wherein said friction means for each disk further comprises an annulus of high-friction material, concentric with the disk, having a radius substantially less than that of the disk, and affixed to the disk between the disk and the base.

14. The reminder in accordance with claim 11, wherein said friction means for each disk further comprises an annulus of high-friction material, concentric with the disk, having a radius substantially less than that of the disk, and affixed to the base between the disk and the base.

15. A blood self-test reminder, used in conjunction with the drawing of blood from the one or more test areas on the fingers of the hand, comprising:

means for representing one or more human hands, containing one or more exposure areas on each finger of each hand representation;

means for designating each said exposure areas as "used" or "unused";

means for retaining each such designation; and means for changing each such designation.

so that the user use the reminder to remind him or her of which fingers have already been tested.

16. The reminder of claim 15, wherein all said means comprise electronic means.

* * * * *